(12) United States Patent
Barnett et al.

(10) Patent No.: US 6,426,417 B1
(45) Date of Patent: Jul. 30, 2002

(54) PROCESSES AND INTERMEDIATES USEFUL TO MAKE ANTIFOLATES

(75) Inventors: Charles Jackson Barnett, Indianapolis; Steven Eugene Dunlap, Fishers; Michael Edward Kobierski, Greenwood; John Arnold Werner, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/601,707

(22) PCT Filed: Jan. 27, 1999

(86) PCT No.: PCT/US99/01689

§ 371 (c)(1),
(2), (4) Date: Aug. 2, 2000

(87) PCT Pub. No.: WO99/41230

PCT Pub. Date: Aug. 19, 1999

Related U.S. Application Data

(60) Provisional application No. 60/074,327, filed on Feb. 11, 1998.

(51) Int. Cl.$^7$ ............................................. C07D 471/02
(52) U.S. Cl. ..................................................... 544/279
(58) Field of Search ........................................ 544/279

(56) References Cited

U.S. PATENT DOCUMENTS

| | | | | |
|---|---|---|---|---|
| 4,927,828 A | * | 5/1990 | Taylor et al. | 514/258 |
| 4,996,206 A | | 2/1991 | Taylor et al. | 514/258 |
| 5,028,608 A | | 7/1991 | Taylor et al. | 514/258 |
| 5,248,775 A | | 9/1993 | Taylor et al. | 544/280 |
| 5,344,932 A | | 9/1994 | Taylor | 544/280 |
| 5,473,071 A | * | 12/1995 | Taylor et al. | 548/279 |
| 5,536,724 A | | 7/1996 | Degraw et al. | 514/258 |

FOREIGN PATENT DOCUMENTS

| | | |
|---|---|---|
| EP | 0 343 801 A2 | 11/1989 |
| JP | 51113874 | 10/1976 |
| JP | 55000730 | 1/1980 |

OTHER PUBLICATIONS

C. J. Barnett, et al., *Tetrahedron Letters*, 38:5, pp. 735–738 (1997).
D.M. Lemal, et al., *Tetrahedron Letters*, vol. 19, p. 1119–1126 (1963).
J.J. Vanden Eynde, et al., *Tetrahedron Letters*, 51:23, pp. 6511–6516 (1995).
E. D. Edstrom, et al., *Tetrahedron Letters*, 36:39, pp. 7035–7038 (1995).
Y. K. Shim, et al., *Synthesis*, vol. 9, pp. 753–754 (1990).
U. Eisner, et al., *J. Chem. Soc.*, pp. 3749–3754 (1955).
N. K. Mohamed, et al., *J. Prakt. Chem., Chem.–Ztg.*, 338:8, pp. 745–749 (1996).
L. Hevesi, et al., *Synthetic Metals*, vol. 59, pp. 201–210 (1993).
P. DeRuggieri, et al., *Chemical Abstract*, 63 10023 (1965).
C. Shih, et al., *Chem. Biol. Pteridines*, 1989 Proc. Int. Symp. Pteridines Folic Acid Deriv., 9$^{th}$, pp. 177–180 (1990).
D. Walker, et al., *Chem. Rev.*, vol. 67, pp. 153, 180–181 (1967).
G. Moad, et al., *J. of Am. Chem. Soc.*, 101:20, pp. 6068–6076 (1979).
M.N. Preobrazhenskaya, et al., *J. of Carbohydrates, Nucleosides, Nucleotides*, 1:5–6, pp. 469–476 (1974).
I.V. Ivleva, et al., *Vestn. Mosk. Univ., Ser. 2, Khim.*, 33:3, pp. 251–255 (1992).

* cited by examiner

*Primary Examiner*—Brenda Coleman
(74) *Attorney, Agent, or Firm*—Elizabeth A. McGraw; Gilbert T. Voy

(57) ABSTRACT

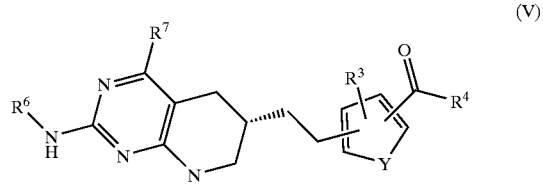

(V)

The present invention concerns intermediates, and processes directed to and from those intermediates, to a series of pyrimidine derivatives of formula (V), which are intermediates to useful antifolate compounds or are themselves useful antifolate compounds.

11 Claims, No Drawings

PROCESSES AND INTERMEDIATES USEFUL TO MAKE ANTIFOLATES

This application is a national stage entry under 35 U.S.C. §371 of PCT/US99/01689, filed Jan. 27, 1999 which claims the benefit of U.S. Provisional Application No. 60/074,327 filed Feb. 11, 1998.

This invention relates to synthetic organic chemistry. Specifically, the invention relates to a process for preparing intermediates useful in the syntheses of valuable antifolate compounds.

Compounds known to have antifolate activity are well recognized as chemotherapeutic agents for the treatment of cancer. A series of N-(6-amino-(pyrrolo(2,3-d)pyrimidin-3-ylacyl)-glutamic acid derivatives of formula V:

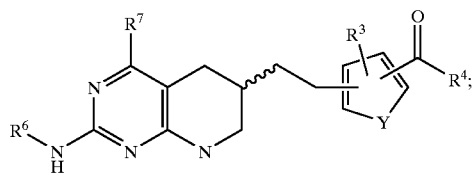

where

Y is CH=CH, O, or S;

$R^3$ is hydrogen, chloro, or fluoro;

$R^4$ is hydroxy, a carboxy protecting group, or NHCH*(C(D)$R^5$)$CH_2CH_2C(O)R^5$;

$R^5$ is hydrogen or a carboxy protecting group;

$R^6$ is hydrogen or an amino protecting group;

$R^7$ is hydroxy or amino; and the configuration about the carbon atom designated * is S; and the pharmaceutical salts thereof were disclosed as antifolates or intermediates to antifolates in U.S. Pat. Nos. 4,684,653 and 4,882,334.

A key step in the synthesis of the compounds of formula V, disclosed in U.S. '334 and '653, is the hydrogenation of compounds of formula VI:

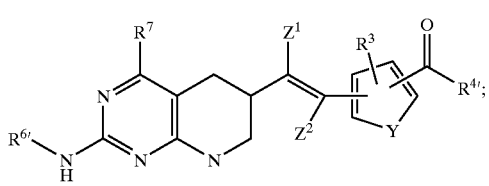

where $Z^1$ and $Z^2$ are both hydrogen or taken together form a bond; $R^{4'}$ is a carboxy protecting group or NHC*H(C(O)$R^{5'}$)$CH_2CH_2C(O)R^{5'}$;

$R^{5'}$ is a carboxy protecting group; and $R^{6'}$ is an amino protecting group;

providing the isomeric mixture of compounds of formula V(a):

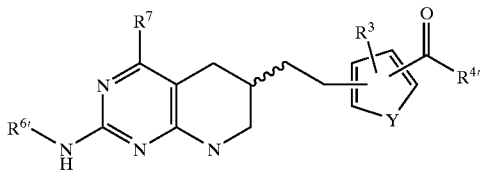

The resulting compound of formula V(a) can optionally have its protecting groups removed to give an isomeric mixture of the compounds of formula V. U.S. '334 and '653 further taught that the individual diastereomers of formula V could be separated mechanically by chromatography or preferably the individual diastereomers could be separated by forming diastereomeric salts with chiral acids, such as camphorsulfonic acid, followed by selective crystallization of one of the diastereomers.

U.S. '334 and '653 taught that compounds of formula VI can be obtained by first coupling a compound of formula VII with a compound of formula VIII:

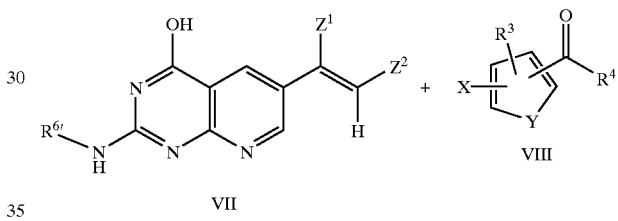

where X is bromo or iodo; in the presence of a palladium/trisubstituted phosphine catalyst of the type described by Sakamoto in *Synthesis*, 1983, 312 et. seq.

The synthesis outlined above suffers in many respects. On an industrial scale, use of a noble metal catalyst is expensive, leads to purification and environmental issues, and can be erratic due to varying amounts of the precious metal that is in the correct oxidation state/complex form for catalysis. Furthermore, if the preferred crystallization separation procedure taught above is followed, after isolating a diastereomer by filtration, the filtrate will contain mixtures of the two diastereomers. This filtrate is often not amenable to further separation by crystallization, and thus separation efficiency suffers without resorting to an undesired chromatographic separation. In certain cases, e.g., where Y is S, $R^3$ is hydrogen, $R^4$ is NHC*H(C(O)$R^5$)$CH_2CH_2C(O)R^5$, and $R^7$ is hydroxy, as much as 80% of the desired isomer (the one with greater antifolate activity) could be found in the filtrate/fractions.

An improvement over the prior art would not rely on precious metal catalysis to produce the compounds of formula VI and would increase the absolute yields of the desired diastereomer of formula VI from mixtures containing both diastereomers by crystallization.

The present invention relates to a compound of formula III:

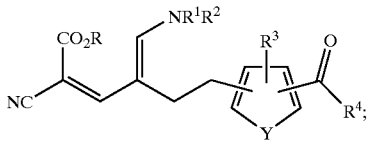

where:
Y is CH=CH, O, or S;
R is $C_1$–$C_6$ alkyl;
$R^1$ and $R^2$ are independently $C_1$–$C_6$ alkyl or taken together with the nitrogen to which they are attached form a heterocycle;
$R^3$ is hydrogen, chloro, or fluoro;
$R^4$ is hydroxy, a carboxy protecting group, or NHC*H(C(O)$R^5$)$CH_2CH_2$C(O)$R^5$ where the configuration about the carbon atom designated * is S; and
$R^5$ is hydrogen or a carboxy protecting group; or a salt or solvate thereof.

The present invention also relates to a compound of formula IV:

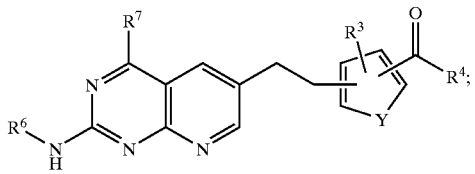

where:
$R^6$ is hydrogen or an amino protecting group; and
$R^7$ is hydroxy or amino; or a salt or solvate thereof.

Moreover, the present invention relates to a process for preparing compounds of formula IV:

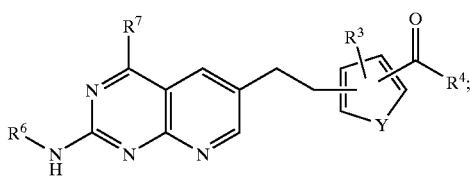

which includes reacting a compound of formula III(a):

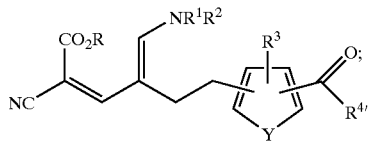

where:
$R^{4'}$ is a carboxy protecting group or NHC*H(C(O)$R^{5'}$)$CH_2CH_2$C(O)$R^{5'}$ where the configuration about the carbon atom designated * is S; and
$R^{5'}$ is a carboxy protecting group;
with 2,4-diamino-6-hydroxypyrimidine in the presence of a suitable acid and solvent.

Furthermore, the present invention also relates to a process for preparing a compound of formula IV, or a salt or solvate thereof, which includes reacting a compound of formula V(b):

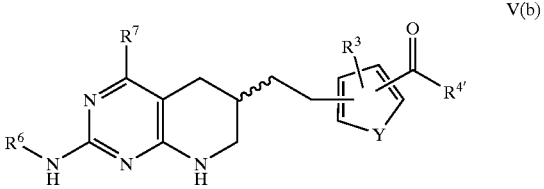

or a salt or solvate thereof, with an oxidizing reagent in the presence of a suitable solvent.

The Compounds

In the general formulae of the present document, the general chemical terms have their usual meanings. For example, the term "$C_1$–$C_4$ alkyl" refers to methyl, ethyl, propyl, isopropyl, cyclopropyl, n-butyl, s-butyl, t-butyl, and cyclobutyl. The term "$C_1$–$C_6$ alkyl" encompasses those listed for $C_1$–$C_4$ alkyl in addition to aliphatic, straight, branched, or cyclic, monovalent moieties having five or six carbon atoms and includes, but is not limited to, pentyl, cyclopentyl, hexyl, cyclohexyl, 2-methylpentyl, and the like. The term "$C_1$–$C_4$ alkoxy" refers to a $C_1$–$C_4$ alkyl group attached through an oxygen atom.

The term "halo" or "halide" refers to chloro, bromo, or iodo.

The term "heterocycle" refers to a 5 or 6 membered saturated, partially unsaturated, or aromatic heterocyclic ring which contains a nitrogen atom and may optionally contain an additional heteroatom selected from N, S, or O.

The term "carboxy protecting group" refers to a substituent of a carbonyl that is commonly employed to block or protect the carboxy functionality while reactions are carried out on other functional groups on the compound.

This substituent, when taken with the carbonyl to which it is attached, may form an ester, e.g., $C_1$–$C_6$ alkyl, substituted $C_1$–$C_6$ alkyl, $C_2$–$C_6$ alkenyl, substituted $C_2$–$C_6$ alkenyl, benzyl, substituted benzyl, benzhydryl, substituted benzhydryl, trityl, substituted trityl, and trialkylsilyl ester. The exact species of carboxy protecting group is not critical so long as the derivatized carboxy group is stable to the conditions of subsequent reaction(s) and can be removed at the appropriate point without disrupting the remainder of the molecule. When $R^4$ contains a carboxy protecting group, the protecting group is preferably $C_1$–$C_4$ alkoxy or benzyloxy. The most preferred protecting groups are methoxy, ethoxy, and benzyloxy. A carboxy protecting group "removable by catalytic hydrogenation" includes, for example, benzyl protecting groups. Other examples of these groups are described in T. W. Greene, "Protective Groups in Organic Synthesis," John Wiley and Sons, New York, N.Y., (2nd ed., 1991), (hereafter referred to as Greene) chapter 5.

The term "$C_2$–$C_6$ alkenyl" refers to a mono-unsaturated, monovalent, hydrocarbon moiety containing from 2 to 6 carbon atoms which may be in a branched or straight chain configuration. The term is exemplified by moieties such as, but not limited to, ethylenyl, propylenyl, allyl, butylenyl, and pentylenyl.

The terms "substituted $C_1$–$C_6$ alkyl" and "substituted $C_2$–$C_6$ alkenyl" refer to a $C_1$–$C_6$ alkyl and $C_2$–$C_6$ alkenyl group respectively substituted from 1 to 3 times independently with a halo, phenyl, tri($C_1$–$C_4$ alkyl)silyl, or a substituted phenylsulfonyl group.

The terms "substituted benzyl", "substituted benzhydryl", and "substituted trityl" refers to a benzyl, benzhydryl, and trityl group, respectively, substituted from 1 to 5 times independently with a nitro, $C_1$–$C_4$ alkoxy, $C_1$–$C_6$ alkyl, or a hydroxy($C_1$–$C_6$ alkyl) group. These substitutions will only occur in a sterically feasible manner such that the moiety is chemically stable.

The term "trialkylsilyl" refers to a monovalent silyl group substituted 3 times independently with a $C_1$–$C_6$ alkyl group.

The term "substituted phenylsulfonyl" refers to a henylsulfonyl group where the phenyl moiety is para ubstituted with a $C_1$–$C_6$ alkyl, nitro, or a halo group.

The term "amino protecting group" as used in the specification refers to a substituent of the amino group commonly employed to block or protect the amino functionality while reacting other functional groups on the compound. The amino protecting group, when taken with the nitrogen to which it is attached, can form a cyclic imide, e.g., phthalimido and tetrachlorophthalimido; a carbamate, e.g., methyl, ethyl, and 9-fluoroenylmethylcarbamate; or an amide, e.g., N-formyl and N-acetylamide. The exact genus and species of amino protecting group employed is not critical so long as the derivatized amino group is stable to the condition of subsequent reaction(s) on other positions of the intermediate molecule and can be selectively removed at the appropriate point without disrupting the remainder of the molecule including any other amino protecting group(s). In general, amino protecting groups removable by acid hydrolysis, i.e., those that are acid labile, are preferred. Thus, a preferred amino protecting groups is 2,2-dimethyl-1-oxopropyl. Further examples of groups and methods referred to by the above terms are described in Greene at chapter 7.

The term "pharmaceutical salt" and "salt" as used herein, refers to salts prepared by reaction of the compounds of the present invention with a mineral or organic acid (e.g., hydrochloric, hydrobromic, hydroiodic, or p-toluenesulfonic acid) or an inorganic base (e.g., sodium, potassium, lithium, and magnesium hydroxide, carbonate, or bicarbonate). Such salts are known as acid addition and base addition salts. For further exemplification of these salts, see, e.g., Berge, S. M, Bighley, L. D., and Monkhouse, D. C., *J. Pharm. Sci.*, 66, 1, 1977.

The term "solvate" represents an aggregate that comprises one or more molecules of a solute, such as a formula III or IV compound, with one or more molecules of solvent.

Reagents

The term "suitable solvent" refers to any solvent, or mixture of solvents, inert to the ongoing reaction that sufficiently solubilizes the reactants to afford a medium within which to effect the desired reaction.

The term "suitable acid" refers to an acid whose $K_a$ is low enough to effect the desired reaction without significantly effecting any undesired reactions.

The term "oxidizing reagent" refers to a reagent whose oxidation potential is high enough to effect the desired reaction without significantly effecting any undesired reactions. Suitable oxidants include metals such as nickel, palladium, platinum, and the like; metals on solid supports such as palladium or platinum on carbon, and the like; metal complexes such as mercury(II), manganese dioxide, or coppor(II) acetate, and benzoquinone based oxidants such as 2,3-dichloro-5,6-dicyano-1,4-benzoquinone (DDQ) and tetrachloro-1,4-benzoquinone (chloranil), and the like.

The term "thermodynamic base" refers to a base which provides a reversible deprotonation of an acidic substrate or is a proton trap for those protons that may be produced as byproducts of a given reaction, and is reactive enough to effect the desired reaction without significantly effecting any undesired reactions. Examples of thermodynamic bases include, but are not limited to, acetates, acetate dihydrates, carbonates, bicarbonates, $C_1$–$C_4$ alkoxides, and hydroxides (e.g., lithium, sodium, or potassium acetate, acetate dihydrate, carbonate, bicarbonate, $C_1$–$C_4$ alkxoxide, or hydroxide), tri($C_1$–$C_4$ alkyl)amines, or aromatic nitrogen containing heterocycles (e.g., imidazole and pyridine).

Synthesis

The compounds of formula III may be prepared from compounds of formula I and II as illustrated in Scheme 1 below where Lg is chloro, bromo, iodo, $OSO_2Me$, $OSO_2$-phenyl, or $OSO_2$-p-toluenyl and R, $R^1$, $R^2$, $R^3$, $R^4$, $R^{4'}$, and Y are as defined above.

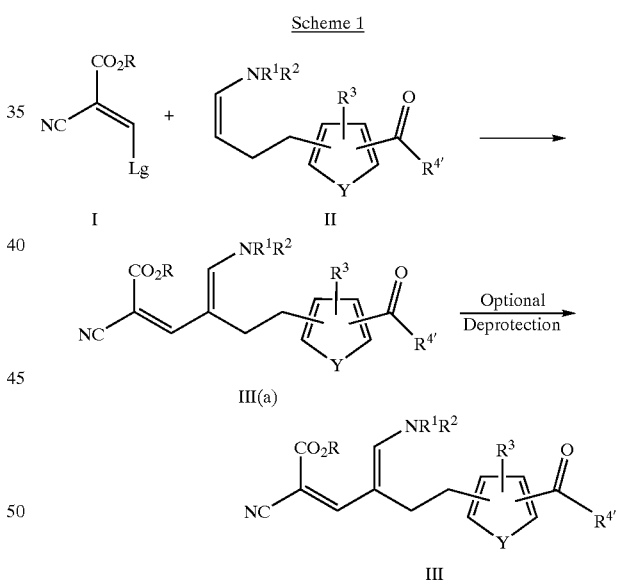

Scheme 1

Compounds of formula I, may be added to compounds of formula II dissolved or suspended in a suitable solvent, in the presence of a thermodyanamic base, to form the compounds of formula III(a). A preferred and convenient solvent is dichloromethane. A preferred and convenient base is triethylamine. A single equivalent of base and compound of formula I, relative to the compound of formula II, is preferably employed but slight excesses on the order of 0.01 to 0.1 equivalents are tolerable. The reaction may be performed between −78° C. and ambient temperature but is preferably performed between −25° C. and −20° C. The reaction is typically complete in from 30 minutes to 18 hours but when performed at the preferred temperature, it is complete in from 1 to 3 hours. A preferred halide in compounds of formula I is chloride. R is preferably $C_1$–$C_4$ alkyl, especially methyl or ethyl. $R^1$ and $R^2$ are preferably $C_1$–$C_4$ alkyl but it is especially preferred when both are either methyl or ethyl. It is preferred that $R^{4'}$ is a carboxy protecting group where that protecting group is $C_1$–$C_4$ alkoxy, especially methoxy or ethoxy, or one capable of being removed by catalytic hydrogenation, e.g., benzyloxy (as in Scheme 3 below). Throughout this specification, $R^3$ is preferably hydrogen and Y is preferably CH=CH or S.

Although the resulting compound of formula III(a) may have its carboxy protecting group removed as taught in Greene, for the purposes of conducting the overall process of Schemes 1–3, the carboxy protecting is preferably left intact when proceeding to the reaction(s) of Scheme 2.

Compounds of formula IV may be prepared from compounds of formula III(a) by the novel process illustrated in Scheme 2 below where R, $R^1$, $R^2$, $R^3$, $R^4$, $R^{4'}$, $R^6$, $R^7$, and Y are as defined above.

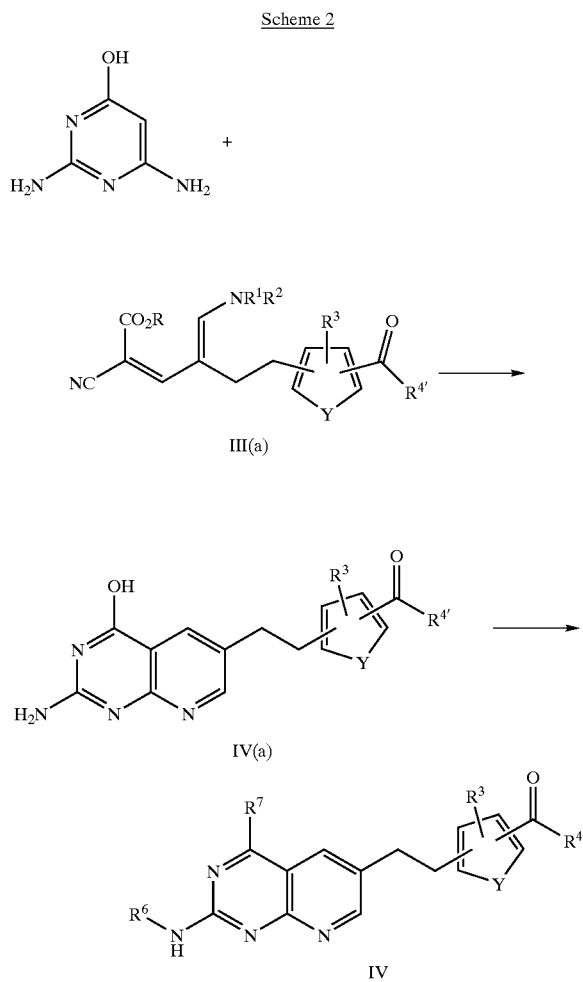

Scheme 2

A tautomeric mixture of 2,4-diamino-6-hydroxypyrimidine or 2,4-diaminopyrimidin-6-one (hereafter referred to as 2,4-diamino-6-hydroxypyrimidine) may be added to a compound of formula III(a), dissolved or suspended in a suitable solvent, in the presence of a suitable acid, to provide the compounds of formula IV(a). A convenenient and preferred solvent is an approximately 1:1 (v:v) mixture of acetonitrile and water. The ratio of acetonitrile to water is not critical but it is preferred that the ratio is amenable to forming a solution when the reactants are all initially combined. A convenient and preferred acid is acetic acid. The acid is typically employed in molar excess. For example, about 2 to about 4 equivalents, relative to the compound of formula III(a), is generally employed while 3 equivalents are typically preferred. The number of equivalents of 2,4-diamino-6-hydroxypyrimidine employed relative to the compound of formula III(a) is not critical but about 1 to about 2 equivalents are preferred. An even more preferred amount is about 1 to about 1.5 with about 1 to about 1.1 equivalents most preferred. The reaction may be performed at temperatures ranging from room temperature to the reflux temperature of the mixture but is preferably performed at the reflux temperature of the mixture. Furthermore, the reaction may take from 12 to about 48 hours depending on the temperature of the reaction. When the reaction is performed at the reflux temperature of the mixture, it is typically substantially complete in about 18 hours. R is preferably $C_1$–$C_4$ alkyl, especially methyl or ethyl. $R^1$ and $R^2$ are preferably $C_1$–$C_4$ alkyl but it is especially preferred when both are either methyl or ethyl. $R^3$ is preferably hydrogen. As stated previously, it is preferred that $R^{4'}$ is a carboxy protecting group where that protecting group is a $C_1$–$C_4$ alkoxy group, especially methoxy or ethoxy, or one capable of being removed by catalytic hydrogenation (as in Scheme 3).

The compounds of formula IV where $R^7$ is an amino group may be prepared from the compounds of formula IV(a) as taught in the previously incorporated by reference U.S. Pat. No. 4,882,334 but it is preferred that $R^7$ is hydroxy.

The compounds of formula IV where $R^6$ is an amino protecting group may be prepared from compounds of formula IV(a) as taught in Greene or as discussed in Preparation 8 below. Furthermore, it is necessary that an amino protecting group, preferably one removable by acid hydrolysis as in Scheme 5 below, e.g., 2,2-dimethyl-1-oxopropyl be present at $R^6$ or that the amino group be protonated before proceeding to the hydrogenation described in Scheme 3 below. Moreover, although the compounds of formula IV(a) may have their carboxy protecting groups removed as taught in Greene, for the purposes of conducting the overall process of Schemes 2–3, it is preferred that the carboxy protecting group is left intact when proceeding to the reaction of Scheme 3.

An isomeric mixture of compounds of formula V(b) may be prepared from compounds of formula IV(b) as illustrated in Scheme 3 below where $R^3$, $R^4$, $R^{6'}$, $R^7$, and Y are as defined above.

Scheme 3

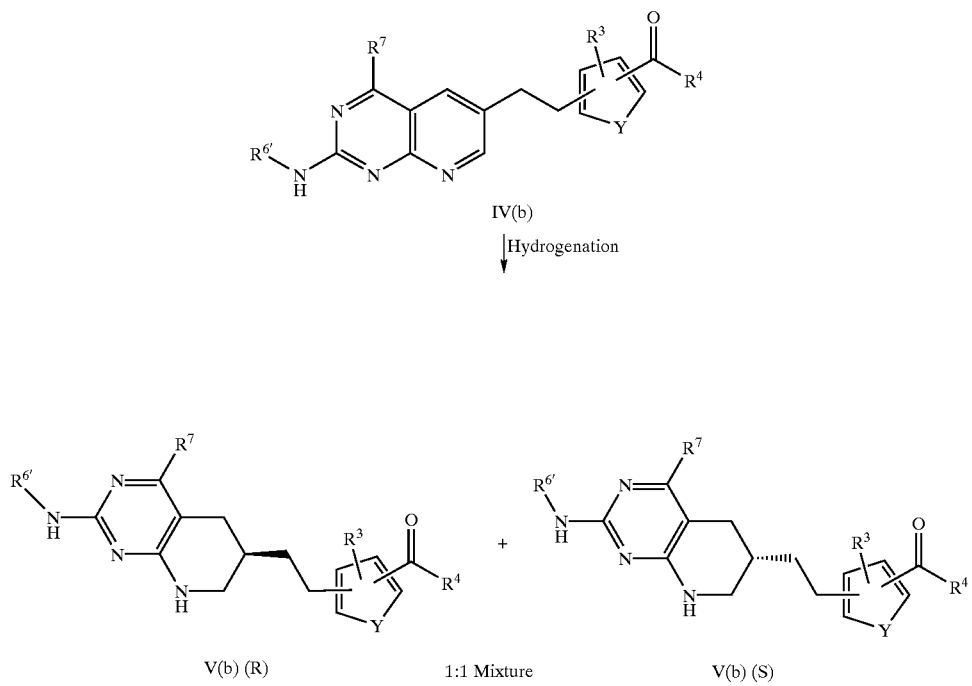

Compounds of formula IV(b), prepared as described in Schemes 1 and 2, may be hydrogenated substantially as described in U.S. Pat. Nos. 4,684,653 and 4,882,334, the teachings of each are hereby incorporated by reference. For facilitation of cross reference, the compounds of formula IV(b) in the present invention correspond to the compounds of formula III in U.S. '653 and the compounds of formula II in U.S. '334. It is preferred that the amino protecting group at $R^{6'}$ is not removed as taught in Greene but left intact when continuing to the separation procedures discussed in Schemes 4 and 5 below.

If the process of Scheme 3 is performed with the compounds of formula IV(b) with the preferred group at $R^4$, i.e., a carboxy protecting group, and that carboxy protecting group is removable by catalytic hydrogenation, then that protecting group will be removed by the hydrogenation conditions of the reaction of Scheme 3. That removal, forming the compounds of formula V(b) where $R^4$ is hydroxy, facilitates the installation of the $R^4$ group found in the antifolate final products, i.e., the chiral glutamic acid, discussed below.

Compounds of formula V which possess antifolate activity are those where $R^4$ is $NHC^*H(C(O)R^5)CH_2CH_2C(O)R^5)$ and $R^6$ is hydrogen (hereafter referred to as "final products"), and thus, those compounds are preferred. Although the glutamate side chain can be installed at any point in the overall process of this invention, when the processes of Schemes 1, 2, 3 are performed in sequence, with the preferred groups noted above, a preffered time to install the glutamate residue is after performing the hydrogenation described in Scheme 3. This is accomplished by coupling a compound of formula V or V(b) where $R^4$ is hydroxy with a carboxy protected glutamic acid derivative of the formula $H_2NC^*H(C(O)R^{5'})CH_2CH_2C(O)R^{5'}$, in the manner generally described in PCT application WO 86/05181, utilizing conventional condensation techniques for forming peptide bonds. These techniques include activation of the carboxy group through formation of a mixed anhydride or acid chloride, treatment with dicyclohexylcarbodiimide, or use of diphenylchlorophosponate. For further instruction on general methods of forming this amide bond, see, e.g., Bodanszky, M., *Principles of Peptide Synthesis*, $2^{nd}$ Ed., Springer-Verlag, Berlin, Heidelberg, 1993. It is preferred that the glutamate side chain is present and that the $R^5$ groups found in that side chain are both carboxy protecting groups, e.g., $C_1$–$C_6$ alkoxy, when performing the processes of Schemes 4 and 5. All discussions and structures pertaining to Schemes 4 and 5 below relate to the situation where the preferred substituents at $R^4$ are present but those substituents are not required for the processes of Scheme 4 and 5 to be operable.

Of the final product compounds of formula V, the compounds of formula V(c)(R), shown below, are preferred due to enhanced antifolate activity relative to the compounds of formula V(c)(S). These individual diastereomeric final products, prepared as described above or in the previously incorporated by reference U.S. Pat. Nos. 4,684,653 and 4,882,334, may be separated as taught in those patents, i.e., by chromatography or preferably recrystallization. For example, an appropriately selected chiral acid may be employed to form a mixture of diastereomeric salts more amenable to selective recrystallization of one diastereomer as illustrated in Scheme 4 below where $R^3$, $R^{5'}$, $R^6$, $R^7$, and Y are as defined above.

Scheme 4

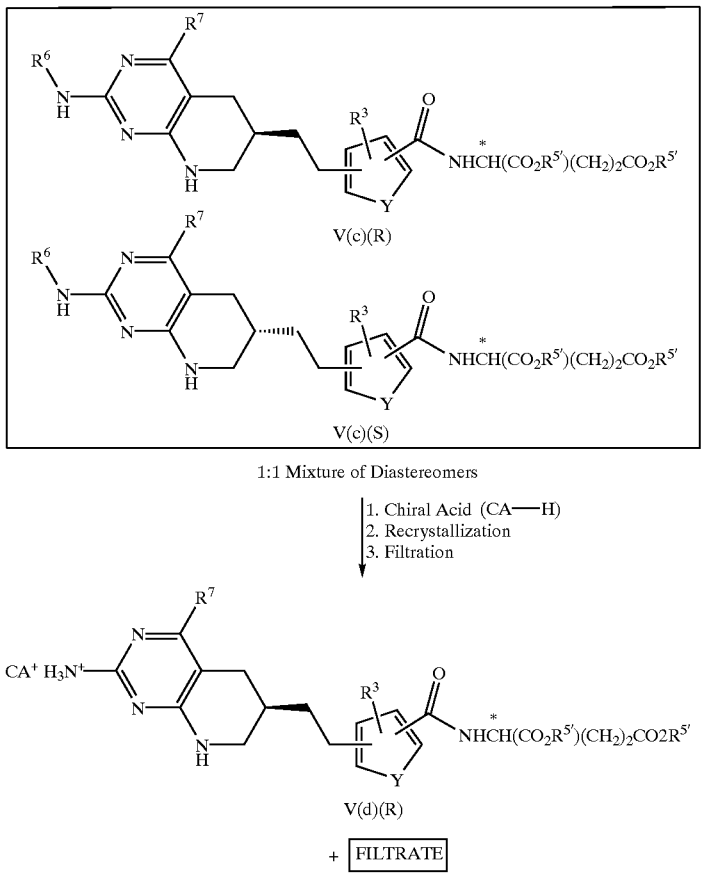

In order to carry out the separation of Scheme 4, it is necessary that $R^6$ in compounds of formula V(c) is hydrogen. If the process of Scheme 4 is performed with the preferred group at $R^6$, i.e., a protecting group removable by acid hydrolysis such as 2,2-dimetyl-1-oxopropyl, then that protecting group will be removed by the addition of the chiral acid and a separate step to remove it will not be necessary. Thus, compounds of formula V(c) where $R^6$ is hydrogen do not necessarily have to be prepared in a separate step before proceeding to the resolution process of Scheme 4. The elimination of the requirement for this extra step is why acid labile amino protecting groups are preferred.

The first step in Scheme 4 is the addition of a chiral acid to a mixture of compounds of formula V(c) dissolved or suspended in a suitable solvent. This addition performs two functions: the chiral acid removes the amino protecting group at $R^6$ and forms a diastereomeric acid addition salt of the compound of formula V(d). When Y is CH=CH, a preferred acid for this purpose is (1S)-(+)-camphorsulfonic acid. When Y is O or S, a preferred acid is (1R)-(−)-camphorsulfonic acid. A preferred solvent for the removal of the protecting group and formation of the salt is a lower alcohol preferably ethanol.

Once the salt is formed, the separation or recrystallization of Step 2 is performed by suspending the compounds of formula V(d) in a suitable solvent, heating the mixture until a solution is formed, and then allowing the solution to cool in order to precipitate the desired isomer. The important parameters in a chiral resolution in general, and when specifically resolving the compounds of formula V(d), are the solvent system, stir rate, and temperature. Preferred solvent systems are mixtures of a lower alcohol, preferably ethanol, and water. The ratio of ethanol to water by volume can be from about 0.33 to about 3 to 1, but a 1:1 mixture is preferred. The ratio of solvent to solute should be about 10 to about 20 to 1 but the preferred ratio is about 15 to 1. The rate of stirring during crystallization can have a marked effect on the resolution. It is preferred that once the salts are formed and dissolved by heating in the crystallization solvent, that the samples are not stirred while cooling. Temperature may also have an impact on resolution. Continued cooling below ambient temperature can increase the recovery of product but at the expense of separation efficiency. It is preferred to allow the crystallization to occur at a temperature between about 20° C. and 34° C. with ambient temperature (about 22° C.) being most preferred.

In order to avoid hydrolysis of the esters on the glutamate residue by the aqueous acidic conditions of the resolution, a buffer such as sodium acetate is preferably employed. An amount of sodium acetate approximately equal to the excess of the acid is preferably added after solvolysis of the amino protecting group is complete.

The filtrate produced in Scheme 4 will contain a mixture of diastereomeric salts of formula V(d). This mixture is enhanced with the diastereomer of formula V(d)(S), i.e., the acid addition salt of V(d)(S), that didn't crystallize. This enhanced mixture is not usually amenable to further separation by crystallization. Thus, a large majority of the desired isomer was heretofore unrecoverable by further crystallization. Scheme 5 below, where $R^3$, $R^{4'}$, $R^6$, $R^7$, and Y are as defined above, illustrates another novel method of preparing compounds of formula IV which facilitates the further separation of this mixture by crystallization.

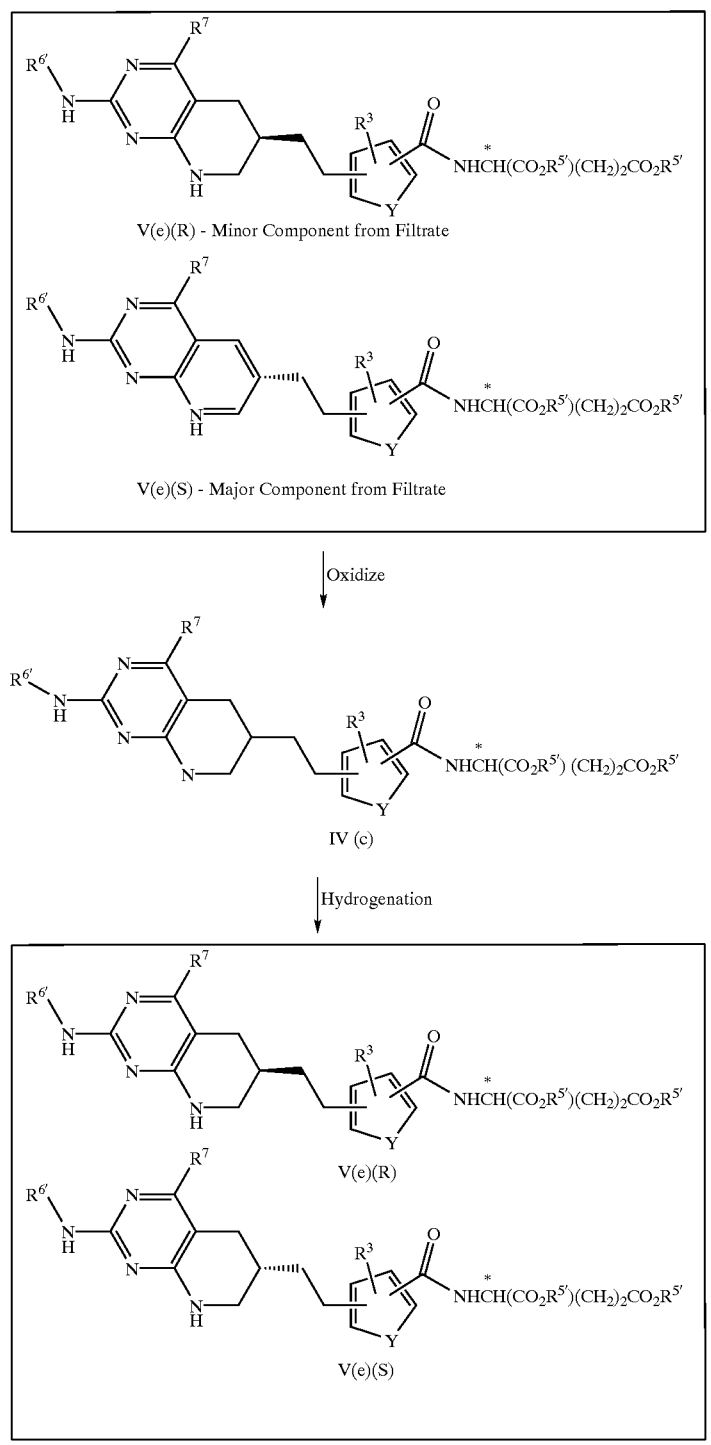

If the process of Scheme 5 is to be performed using the contents of the filtrate from Scheme 4 as a source of starting materials, it is preferred that the free base compounds of formula V(c) are first extracted from that mixture. This is easily accomplished by diluting the mixture with a water immiscible organic solvent and treating the mixture with a weak base dissolved in water such as a solution of sodium bicarbonate in water. Dichloromethane and aqueous sodium bicarbonate are preferred reagents for this purpose. For example, treatment of the filtrate with dichloromethane (about 0.33 mL/g filtrate) and about 2 equivalents of 1M aqueous sodium bicarbonate for about 30 minutes at room temperature will afford two clear, readily-separable phases. The organic phase is separated and preferably dried with a common drying agent or agents before proceeding. Sequential washes with brine and 1M aqueous sodium bicarbonate is a preferred drying procedure.

Once the extraction procedure is performed, an amino protecting group must be reinstalled at $R^6$ or that amino group must be protonated before performing the process illustrated in Scheme 5. Reprotection is preferred and may be accomplished as taught in Greene cited above or as discussed in Preparation 9 below. It is preferred that the amino protecting group be removable by acid hydrolysis, e.g., a 2,2-dimethyl-1-oxopropyl protecting group. The resulting compounds of formula V(e) are then separated as follows.

Single diastereomers or mixtures of any ratio of compounds of formula V(e) may be dissolved or suspended in a suitable solvent and an oxidizing reagent added to provide the compounds of formula IV(b). Choice of solvent, reaction temperatures, and times will depend generally on the oxidizing reagent employed.

DDQ is a preferred oxidizing agent. When DDQ or chloroanil is employed as the oxidizing agent, hydrocarbons such as pentane, hexane, toluene, and the like; lower alcohols such as methanol, ethanol, isopropanol, and the like; or chlorinated hydrocarbons such as chloroform, dichloromethane, and the like; are suitable. Chlorinated hydrocarbons, especially dichloromethane, are preferred. When the oxidation is performed under the preferred conditions on the preferred compounds of formula V(e), chromatography to purify the resulting compounds of formula IV(b) is generally not necessary. See, e.g., Example 6 below.

The reaction is typically allowed to proceed at temperatures between 0° C. and 200° C. for from about 30 minutes to about 24 hours. The reaction is preferably performed at temperatures between 15° C. to 80° C. Even more preferred is when the reaction is performed between 20° C. to 40° C., and most preferred is when the reaction is performed at room temperature for from 20 minutes to 1 hour.

The amount of oxidizing reagent will vary depending on which oxidant is employed but will generally range from about 0.1 equivalents to about 5 equivalents relative to the compound of formula V(e). When DDQ is employed, about 1.1 to about 3 equivalents are preferred. Even more preferred is from 1.8 to about 2.2 equivalents while 1.9 to about 2.1 equivalents is most preferred.

The carboxy and/or amino protecting groups in compounds of formula IV(b) are preferably not removed as taught in Greene. Instead, a preferred course of action is to reduce the compounds of formula IV(b) back to a 50:50 diastereomeric mixture of compounds of formula V(e) in order to perform the chiral acid separation taught in Scheme 4.

The hydrogenation may be performed by dissolving or suspending a compound of formula IV(b) in a suitable solvent, in the presence of a hydrogenation catalyst, and exposing the mixture to an atmosphere of hydrogen. A convenient and preferred solvent is about a 4:1 mixture by volume of tetrahydrofuran and ethanol. A convenient and preferred hydrogenation catalyst is 5% palladium on carbon. The catalyst is typically employed, relative by weight to compounds of formula IV(b), in a range of from about 10% to about 200%. Preferably, the range is from about 20% to about 75%, with about 25% being preferred. It is typically preferred to create an atmosphere of hydrogen where the pressure of hydrogen is equal to or greater than that of ambient pressure. A typical pressure range is from about ambient to about 100 psi of hydrogen. More preferred is an atmosphere of hydrogen between 40 psi and about 60 psi with 50 psi most preferred. The reaction may be performed at temperatures ranging from ambient to about the reflux temperature of the mixture. At 50 psi of hydrogen, the preferred reaction temperature is about 100° C., with the reaction typically substantially complete in less than 4 hours.

Once a 1:1 mixture of compounds of formula V(e) is formed as described in Scheme 5, it is further amenable to separation as discussed in Scheme 4 above. This cycle may be repeated as many times as the practitioner wishes in order to maximize the yield of the diastereomer of formula V(d) (R).

2,4-Diamino-6-hydroxypyrimidine, protected glutamic acids of the formula $H_2NC^*H(C(O)R^{5'})CH_2CH_2C(O)R^{5'}$ and compounds of formula I and II are known in the art, and, to the extent not commercially available are readily synthesized by standard procedures commonly employed in the art. For example, see Preparations 1–6 below.

The optimal time for performing the reactions of Schemes 1–5 can be determined by monitoring the progress of the reaction by conventional chromatographic techniques. Choice of solvent is generally not critical so long as the solvent employed is inert to the ongoing reaction and sufficiently solubilizes the reactants to afford a medium within which to effect the desired reaction. Unless otherwise indicated, all of the reactions described herein are preferably conducted under an inert atmosphere. A preferred inert atmosphere is nitrogen.

The following preparations and examples are illustrative only and are not intended to limit the scope of the invention in any way. The terms and abbreviations used in the instant examples have their normal meanings unless otherwise designated. For example "° C.", "N", "mmol", "g", "mg", "d.e.", "mL", "M", "HPLC", "mp", "EA", "MS(FD)", "MS (HR)", "IR", and "$^1$H NMR", refers to degrees Celsius, normal or normality, millimole, gram, milligram, diastereomeric excess, milliliter, molar or molarity, high pressure liquid chromatography, melting point, elemental analysis, field desorption mass spectrometry, high resolution mass spectrometry, infrared spectroscopy, and proton nuclear magnetic resonance spectroscopy respectively. In addition, the absorption maxima listed for the IR spectra are only those of interest and not all of the maxima observed.

PREPARATION 1

5-(3-[1,3-Dioxolan-2-yl]propyl)-2-thiophene Carboxylic Acid

To a solution of 64.8 g (640 mmol, 83.9 mL) of diisopropyl amine in 400 mL of tetrahydrofuran which had been cooled to −15° C. was added 400 mL (640 mmol) of 1.6M n-butyllithium in hexane dropwise over 25 minutes, maintaining the reaction temperature below −5° C. After a 15 minute stir time, a solution of 5-methyl-2-thiophenecarboxylic acid (41.4 g, 291 mmol) in 150 mL of tetrahydrofuran was added dropwise over 30 minutes, once again keeping the temperature below −5° C. The resultant dark green dianion solution was stirred at −15° C. to −10° C. for 90 minutes. To this solution was added 2-(2-bromoethyl)-1,3-dioxolane (57.9 g, 320 mmol) dropwise over 15 minutes and the magenta-colored mixture was stirred for 3 hours at −10° C. to −5° C. HPLC analysis (30% acetonitrile/70% 1% aqueous acetic acid solution, 2 mL/min, 30 cm C-18 column, λ=280 nm) at this time showed 9.0% 5-methyl-2-thiophenecarboxylic acid and 88.5% title compound. The reaction was quenched with 600 mL of water and acidified to pH 3 with 6N aqueous hydrochloric acid. The yellow mixture was extracted three times with 500 mL of t-butylmethyl ether and the combined organic extracts were dried over magnesium sulfate, filtered, and concentrated. The crude product was triturated with 300 mL of heptane and the solid was filtered, washed with heptane, and pulled dry on the filter to provide 58.21 g (82.5%) of the title compound which contained less than 3% starting material by $^1$H NMR. $^1$H NMR (300 MHz, CDCl$_3$) δ 1.81 (m, 4H), 2.91 (t, J=7.4 Hz, 2H), 3.92 (m, 4H), 4.90 (t, J=4.4 Hz, 1H), 6.84 (d, J=3.7 Hz, 1H), 7.72 (d, J=3.7 Hz, 1H).

PREPARATION 2

Methyl-5-(3-[1,3-Dioxolan-2-yl]propyl)-2-thiophene Carboxylate

To a solution of 5-(3-[1,3-dioxolan-2-yl]propyl)-2-thiophene carboxylic acid (58.0 g, 239 mmol) in 300 mL of dimethylformamide was added potassium carbonate (41.4 g, 299 mmol) followed by methyl iodide (51.0 g, 359 mmol). The slurry was stirred at ambient temperature for 17 hours and then poured into 600 mL of water. The resulting suspension was extracted twice with 500 mL of t-butylmethylether and the combined extracts were washed with water, dried over magnesium sulfate, filtered, and concentrated by rotory evaporation to afford 57.84 g (94.3%) of the title compound which was of sufficient purity for use in Preparation 3. IR (CHCl$_3$, cm$^{-1}$) 3021, 1707, 1541, 1463, 1296, 1101. $^1$H NMR (300 MHz, CDCl$_3$) d 1.75 (m, 4H), 2.84 (t, J=7.4 Hz, 2H), 3.81 (s, 3H), 3.82 (m, 2H), 3.92 (m, 2H), 4.84 (t, J=4.3 Hz, 1H), 6.76 (d, J=3.9 Hz, 1H), 7.58 (d, J=3.7 Hz, 1H).

PREPARATION 3

Methyl-5-(butan-4-al)-2-thiophene Carboxylate

Methyl-5-(3-[1,3-dioxolan-2-yl]propyl)-2-thiophene carboxylate (10.0 g, 39.0 mmol) and 1.0 mL of concentrated hydrochloric acid were dissolved in 120 mL of 2:1 acetic acid/water and the resultant yellow solution was heated in a 60° C. oil bath for 2 hours. The solution was allowed to cool to 25° C. and poured into 120 mL of water. After stirring for 15 minutes, this mixture was extracted twice with 125 mL of t-butylmethylether. The combined organic extracts were washed twice with water and twice with saturated aqueous sodium bicarbonate solution, then dried over magnesium sulfate, filtered, and concentrated to 8.24 g (99.5%) of the title compound which was of sufficient purity for use in Preparation 4. $^1$H NMR (300 MHz, CDCl$_3$) δ 2.01 (m, 2H), 2.50 (t, J=7.4 Hz, 2H), 2.87 (t, J=7.5 Hz, 2H), 3.84 (s, 3H), 6.79 (d, J=3.7 Hz, 1H), 7.61 (d, J=4.0 Hz, 1H), 9.75 (s, 1H).

PREPARATION 4

Methyl-5-(4-diethylaminobut-3-enyl)-2-thiophene Carboxylate

Methyl-5-(butan-4-al)-2-thiophene carboxylate (16.7 g, 78.6 mmol) was cooled to 0° C.–5° C. with stirring and treated with diethylamine (11.5 g, 157 mmol) over 5 minutes. The cooling bath was removed and 27.6 g of potassium carbonate were added in one portion. The orange mixture was heated at 60° C. for one hour and then allowed to cool to 25° C. The reaction mixture was diluted with 50 mL of dichloromethane and filtered through Hyflo®, rinsing well with excess dichloromethane. The filtrate was concentrated to 19.6 g (93.4%) of the title compound which was of sufficient purity for use in Preparation 5. $^1$H NMR (300 MHz, CDCl$_3$) δ 1.01 (t, J=7.1 Hz, 6H), 2.28 (q, J=7.4 Hz, 2H), 2.68 (m, 2H), 2.91 (q, J=7.1 Hz, 4H), 3.89 (s, 3H), 4.12 (m, 1H), 5.84 (d, J=13.9 Hz, 1H), 7.23 (d, J=8.1 Hz, 2H), 7.94 (d, J=8.1 Hz, 2H)

PREPARATION 5

Methyl-hydroxymethylene-cyanoacetate Sodium Salt

Sodium metal (11.8 g, 0.511 mol) was dissolved in 450 mL of methanol and to this warm solution was added a solution of ethyl formate (104 g, 1.41 mol) and methyl cyanoacetate (43.8 g, 0.440 mol) over two minutes. A small amount of precipitate formed during the addition. The reaction mixture was heated to reflux and maintained there for 1.5 hours. The thick white suspension was allowed to cool to 20° C.–25° C. and the precipitate was filtered, washed with diethylether, and dried in vacuo at 45° C. to give 40.4 g (61.6%) of the title compound which was of sufficient purity for use in Preparation 6.

PREPARATION 6

Methyl-chloromethylene-cyanoacetate

To a suspension of the sodium salt of methylhydroxymethylene-cyanoacetate (19.0 g, 127 mmol) in 200 mL of dichloromethane was added phosphorous pentachloride (26.5 g, 127 mmol) in one portion. The reaction mixture was allowed to exotherm to reflux temperature and then maintained at reflux with stirring for 4 hours. The resulting light yellow suspension was allowed to cool to 23° C. and then poured into 400 mL of cold water. The mixture stirred for 15 minutes and the phases were separated. The aqueous layer was extracted with 100 mL of dichloromethane and the combined organic layers were washed twice with water, dried over magnesium sulfate, and concentrated to 16.8 g of the title compound which was of sufficient purity for use in Example 1. $^1$H NMR (300 MHz, CDCl$_3$) δ 3.88 (s, 3H), 7.58 (s, 0.35H), 8.04 (s, 0.65H).

PREPARATION 7

N-[[5-[2-[(6R)-2-Amino-3,4,5,6,7,8-hexahydro-4-oxopyrido-(2,3-d)-pyrimidin-6-yl]ethyl]-2-thienyl]carbonyl]-L-glutamic Acid, Diethyl Ester (1R)-(–)-10-camphorsulfonic Acid Salt (R-R-L)

A mixture of N-[[5-[2-[2-[(2,2-dimethyl-1-oxopropyl)amino)-3,4,5,6,7,8-hexahydro-4-oxopyrido-(2,3-d)-pyrimidin-6-yl]ethyl]-2-thienyl]carbonyl]-L-glutamic acid, diethyl ester (456.1 g, 0.748 mol) and anhydrous (1R)-(–)-10-camphorsulfonic acid (197.6 g, 0.84 mol) in 3.4 L of absolute ethanol was heated under reflux. After 28 hours the reaction was found to be complete by HPLC analysis (C18 column at 40° C., 40:60 acetonitrile:buffer, flow rate 2.0 mL/min, detection at 280 nm, buffer=1:0.3:100 glacial acetic acid:triethylamine:water). The mixture was allowed to cool to 68° C. and 6.34 g of sodium acetate, 3.4 L of water, and 23 g of activated carbon were added. The mixture, cooled to 46° C. by the additions, was allowed to stir for 20 min, then filtered through Hyflo®. The resulting solution was stirred, cooled to 34° C., and seeded. The mixture was allowed to stand at ambient temperature for 12 hours without agitation to allow crystal formation. The crystals were collected by filtration and dried. The filtrate was set aside overnight, causing additional crystallization to occur. The crystals from the filtrate were collected, combined with the first precipitate and dried, affording 292.2 g of the R-R-L title compound. The partially purified salt was recrystallized two times from 15 times its mass of ethanol-water 1:1. There was obtained 101.9 g (35.6% of theory) of the title compound as a monohydrate, 95.4% d.e. by HPLC analysis. mp 207° C.–210° C. MS(FD) m/z 505 (M$^+$); [a]589 –52.8°, [a]365 –267.7° (c 1.0, DMSO). EA calculated for C$_{33}$H$_{47}$N$_5$O$_{10}$S$_2$.H$_2$O (755.90): C, 52.44; H, 6.53 N, 19.26 Found: C, 52.31; H, 6.35; N, 19.20.

PREPARATION 8

Recovery of a 2:3 Mixture of R-L and S-L Diastereomers of N-[[5-[2-[2-Amino-1,4,5,6,7,8-hexahydro-4-oxopyrido[2,3-d]pyrimidin-6-yl)ethyl]-2-thienyl]carbonyl]-L-glutamic Acid, Diethyl Ester From the Filtrate of Preparation 7

A solution of 1M aqueous sodium bicarbonate was added to a stirred mixture of the filtrate from Preparation 7 (1000 g, about 1.93% title compounds (w/w)) and dichloromethane (333 g). The pH was adjusted from 5.0 to approximately 7 with additional 1M aqueous sodium bicarbonate (50.0 g). The resulting mixture was stirred for 1 hour. The phases were separated to give 392.9 g of a clear, yellow organic phase. The solution was washed with 0.5M aqueous sodium bicarbonate (50 g) for 30 minutes. The phases were separated to give 341.3 g of a slightly-cloudy, yellow organic phase. A 5 g retainer sample was removed and the remaining solution washed with a solution of 10% aqueous sodium choride (100 g) for 15 minutes. After a 1 hour phase separation, 293.4 g of the slightly-cloudy, yellow organic phase was isolated. A 5 g retainer sample was removed and the solution was concentrated to a foam by rotary evaporation. The residue was redissolved in dichloromethane (100 g) and concentrated to a foam again. Vacuum drying for 18 hours at 45° C./5 Torr afforded 17.86 g of a yellow foam (90.6% potency of a 36.8:63.2 mixture of the title compounds, respectively, 88.7% recovery based on potency assay of original filtrate, 90.0% recovery based on mass balance of product in aqueous and organic layers). This material was carried into the recycle procedure of Examples 6 and 7 without further purification.

PREPARATION 9

2:3 Mixture of R-L and S-L Diastereomers of N-[[5-[2-[2-[(2,2-Dimethyl-1-oxopropyl)amino)-3,4,5,6,7,8-hexahydro-4-oxopyrido-(2,3-d)-pyrimidin-6-yl]ethyl]-2-thienyl]carbonyl]-L-glutamic Acid, Diethyl Ester Anhydrous pyridine (50.9 g, 642.9 mmol) was added to the 2:3 mixture of R-L and S-L diastereomers of N-[[5-[2-[2-amino-3,4,5,6,7,8-hexahydro-4-oxopyrido-(2,3-d)-pyrimidin-6-yl]ethyl]-2-thienyl]carbonyl]-L-glutamic acid diethyl ester (24.7 g, 49.0 mmol) from Preparation 8 and 4-dimethylaminopyridine (1.49 g, 12.2 mmol). After heating to 100° C. with stirring, a yellow solution persisted. Pivalic anhydride (19.0 g, 102.8 mmol) was added over 4 minutes; with each drop a white solid formed then dispersed. At 4.5 hours the reaction was cooled to 50° C. (caution: solidifies at lower temperature), transferred to a separatory funnel and dichloromethane (500 mL) then 1N aqueous hydrochloric acid (660 mL) were added. The organic layer was separated and extracted with 1N aqueous hydrochloric acid (250 mL), plus dichloromethane (100 mL) to prevent clouding. The resulting organic layer was washed with a brine (200 mL) again requiring additional dichloromethane (100 ml) to prevent clouding, then dried over magnesium sulfate. The solvent was partially removed at 26.5 inches Hg vacuum and 40° C. until evaporation nearly ceased. To the remaining solution, anhydrous diethyl ether (300 mL) was added over 35 minutes to give a white mixture. After 15 minutes stirring, the solid was collected by vacuum filtration, washing twice with diethyl ether (100 mL). Note: the filtrations required 15–30 minutes and were stirred after each addition of diethyl ether. Vacuum drying at 40° C./5 Torr for 2 hours afforded 27.88 g crude product. This residue was refluxed in ethyl acetate (700 mL) until a light yellow solution was obtained. The contents were allowed to equilibrate to room temperature with stirring over 1 hour. The white mixture was placed in an ice bath and stirred 1.5 hours. The product was isolated by vacuum filtration, washing three times with cold ethyl acetate (50 mL) and once with diethyl ether (100 mL). Vacuum drying at 40° C./5 Torr afforded 19.40 g (68%) of the title compound as a white solid. mp 169° C.–170° C. [a]$^{20}_D$ –0.2° (c 1.01, MeOH). EA calculated for C$_{28}$H$_{39}$N$_5$O$_7$S: C, 57.03; H, 6.67; N, 11.88; 0, 18.99; S, 5.44. Found: C, 57.05; H, 6.47; N, 11.66; 0, 19.16; S, 5.66.

EXAMPLE 1

Methyl-5-(3-[2-cyano-2-carboethyoxyethenyl]-4-diethylaminobut-3-enyl)-2-thiophene Carboxylate To a solution of methyl-5-(4-diethylaminobut-3-enyl)-2-thiophene carboxylate (19.4 g, 72.4 mmol) and triethylamine (7.3 g, 72.4 mmol) in 160 mL of dichloromethane cooled to −25° C. was added a solution of methyl-chloromethylene-cyanoacetate (10.5 g, 72.4 mmol) in 40 mL of dichloromethane dropwise over 25 minutes, maintaining the pot temperature below −20° C. The cloudy orange solution was stirred at −25° C. to −20° C. for two hours and then allowed to warm to 20° C. The reaction mixture was diluted with 150 mL of water and the two layers were allowed to stir together for a few minutes and separate. The organic layer was dried over magnesium sulfate, filtered, and concentrated to an orange oil. The oil was triturated with diethyl ether, causing the desired product to crystallize. The resulting solid was filtered, washed with ether and dried to provide 19.6 grams (72%) of the title compound which was of sufficient purity for use in Example 2. MS m/z 377 (M+H). EA calculated for $C_{19}H_{24}N_2O_4S$: C, 60.62; H, 6.43; N, 7.44. Found: C, 61.67; H, 6.85; N, 7.33.

EXAMPLE 2

2-Amino-1,4-dihydro-4-oxopyrido-6-(2-[2-carbomethoxythiophen-5-yl]ethyl)[2,3-d]pyrimidine To a solution of methyl-5-(3-[2-cyano-2-carboethyoxyethenyl]-4-diethylaminobut-3-enyl)-2-thiophene carboxylate (10.0 g, 26.56 mmol) in 50 mL of acetonitrile was added 2,4-diamino-6-hydroxypyrimidine (3.35 g, 26.56 mmol), 45 mL of water, and 5 mL of acetic acid. The resulting suspension was heated to reflux for 18 hours and then allowed to cool to 25° C. The reaction mixture was neutralized to pH 6.7 with 2N aqueous sodium hydroxide causing the precipitate to thicken. The solid was filtered, washed with 1:1 acetonitrile/water, and dried in vacuo at 50° C. to afford 5.96 grams (68%) of the title compound.

EXAMPLE 3

2-Amino-1,4-dihydro-4-oxopyrido-6-(2-[2-carboxythiophen-5-yl]ethyl)[2,3-d]pyrimidine 2-Amino-1,4-dihydro-4-oxopyrido-6-(2-[2-carbomethoxythiophene-5-yl]ethyl)[2,3-d]pyrimidine (5.4 g, 16.35 mmol) was dissolved in 54 mL of 2N aqueous sodium hydroxide and heated to 40° C. with stirring. HPLC analysis (30% acetonitrile/70% of a 1% aqueous acetic acid solution, 1 mL/min, C8 25 cm column, 1=280 nm) showed complete hydrolysis of the methyl ester. The solution was diluted with 81 mL of ethanol and acidified to pH 3 with 6N aqueous hydrochloric acid. The resulting precipitate was filtered, washed with 1:1 ethanol/water, and dried in vacuo at 50° C. to provide 5.02 g (97%) of the title compound as a light yellow solid. $^1$H NMR (300 MHz, DMSO-$d_6$) δ 2.97 (t, J=7.2 Hz, 2H), 3.15 (t, J=7.2 Hz, 2H), 6.89 (d, J=3.6 Hz, 1H), 7.50 (d, J=3.6 Hz, 1H), 8.05 (d, J=2.3 Hz, 1H), 8.45 (d, J=1.8 Hz, 1H).

EXAMPLE 4

2-[(2,2-Dimethyl-1-oxopropyl)amino]-1,4-dihydro-4-oxopyrido-6-(2-[2-carboxythiophen-5-yl]ethyl) [2,3-d]pyrimidine To a suspension of 2-amino-1,4-dihydro-4-oxopyrido-6-(2-[2-carboxythiophen-5-yl]ethyl)[2,3-d]pyrimidine (0.93 g, 2.94 mmol) in 20 mL of pivalic anhydride was added dimethylaminopyridine (0.036 g, 0.294 mmol) and the mixture was heated to 150° C. for 18 hours, during which time the reaction mixture thinned considerably. The reaction was allowed to cool to 25° C. and the product was precipitated by the addition of 100 mL of diethyl ether. The precipitate was filtered with suction and washed with ether. The resulting solid was suspended in 10 mL of water and treated with 1N aqueous sodium hydroxide solution until a solution formed. The solution was acidified to pH 4 with 6N aqueous hydrochloric acid causing the product to precipitate. The solid was filtered, washed with water followed by methanol, and dried in vacuo at 50° C. to afford 0.84 g (71%) of the title compound as a tan solid. $^1$H NMR (300 MHz, DMSO-$d_6$) δ 1.23 (s, 9H), 3.14 (m, 4H), 6.90 (d, J=3.6 Hz, 1H), 7.48 (d, J=3.6 Hz, 1H), 8.27 (s, 1H), 8.70 (s, 1H), 11.37 (bs, 1H), 12.25 (s, 1H).

EXAMPLE 5

N-[[5-[2-[2-[(2,2-Dimethyl-1-oxopropyl)amino]-1,4-dihydro-4-oxopyrido-[2,3-d]-pyrimidin-6-yl]ethyl]-2-thienyl]carbonyl]-L-glutamic Acid, Diethyl Ester To a mixture of 2-[(2,2-dimethyl-1-oxopropyl)amino]-1,4-dihydro-4-oxopyrido-6-(2-[2-carboxythiophen-5-yl]ethyl)[2,3-d]pyrimidine (0.54 g, 1.35 mmol) and N-methylmorpholine (0.41 g, 4.05 mmol) in 5 mL of dimethylformamide was added 2-chloro-4,6-dimethoxy-1,3,5-triazine (0.31 g, 1.75 mmol) in one portion. The resulting suspension was stirred at ambient temperature for 16 hours. At this time, L-glutamic acid diethyl ester (0.36 g, 1.48 mmol) was added and stirring was continued at ambient temperature for 3 hours. The reaction mixture was partitioned between 30 mL of methylene chloride and 30 mL of water, and the two layers were stirred together and allowed to separate. The organic layer was concentrated to an amber oil which was triturated with ethanol, causing a solid precipitate to form. The solid was filtered, washed with ethanol, and dried in vacuo at 50° C. to give 0.59 g (75%) of the title compound. mp 72° C.–76° C. $^1$H NMR (300 MHz, DMSO-$d_6$) d 1.14 (m, 6H), 1.22 (s, 9H), 2.04 (m, 2H), 2.38 (t, J=7.3 Hz, 2H), 3.12 (m, 4H), 4.05 (m, 4H), 4.34 (m, 1H), 6.88 (d, J=3.6 Hz, 1H), 7.63 (d, J=3.7 Hz, 1H), 8.24 (s, 1H), 8.61 (d, J=7.3 Hz, 1H), 8.72 (s, 1H), 10.85 (vbs, 2H).

EXAMPLE 6

N-[[5-[2-[2-[(2,2-Dimethyl-1-oxopropyl)amino]-1,4-dihydro-4-oxopyrido-[2,3-d]-pyrimidin-6-yl]ethyl]-2-thienyl]carbonyl]-L-glutamic Acid, Diethyl Ester Dichloromethane (350 mL) was added to the 2:3 mixture of R-L and S-L diastereomers of N-[[5-[2-[2-[(2,2-dimethyl-1-oxopropyl)amino]-3,4,5,6,7,8-hexahydro-4-oxopyrido-(2,3-d)-pyrimidin-6-yl]ethyl]-2-thienyl]carbonyl]-L-glutamic acid, diethyl ester (17.0 g, 28.9 mmole) from Preparation 9 and stirred 30 minutes until a light yellow solution formed. As a solid, 2,3-dichloro-5,6-dicyano-1,4-benzoquinone (DDQ) (13.4 g, 59.2 mmol) was added. The solution initially turned purple, then with 30 minutes stirring at room temperature it transitioned to a light pink mixture. A pink solid was removed by filtration, washing three times with dichloromethane (25 mL). The filtrate was stirred three times for 30 minutes with a saturated solution of sodium bicarbonate (200 mL) and separated. The final organic layer was stirred for 30 minutes with sodium bicarbonate (100 mL) and water (100 mL) then separated. The organic layer was washed with brine (100 mL) and dried over magnesium sulfate. Removal of the solvent at reduced pressure gave 14.7 g (87.1%) of the title compound. mp 57° C.–87° C. IR(CHCl$_3$): 3690–3025, 2978, 3000, 1736, 1677, 1629, 1558, 1449, 1245, 1147, 1022, 811 cm$^{-1}$. MS(HR) calculated for $C_{28}H_{35}N_5O_7S$: 586.234100. Found: 586.233546.

EXAMPLE 7

1:1 Mixture of R-L and R-S Diastereomers of N-[[5-[2-[2-[(2,2-Dimethyl-1-oxopropyl)amino]-3,4,5,6,7,8-hexahydro-4-oxopyrido-(2,3-d)-pyrimidin-6-yl]ethyl]-2-thienyl]carbonyl]-L-glutamic Acid, Diethyl Ester N-[[5-[2-[2-[(2,2-Dimethyl-1-oxopropyl)amino3-1,4-dihydro-4-oxopyrido-[2,3-d]-pyrimidin-6-yl]ethyl]-2-thienyl]carbonyl]-L-glutamic acid, diethyl ester (1.0 g, 1.8 mmol), 5% palladium on carbon catalyst (0.26 g), ethanol (4.0 mL), and tetrahydrofuran (16.0 mL) were added to a hydrogenation vessel. The resulting mixture was pressurized three times with nitrogen (10 psig) and vented. Then the mixture was pressurized three times with hydrogen (50 psig) and vented. The hydrogen pressure was then adjusted to 50 psig and the temperature increased to 100° C. After 22 hours, with 7% starting material remaining by HPLC, the reaction was allowed to equilibrate to room temperature and the catalyst was removed by filtering through Celite and washing with 4:1 tetrahydrofuran/ethanol. The filtrate was evaporated, redissolved in dichloromethane (25 mL), extracted with aqueous sodium bicarbonate (25 mL), dried over magnesium sulfate, and evaporated. The residue was stirred in ethyl acetate (10 mL) at reflux. After 1 hour the mixture was allowed to cool to room temperature and was then stirred in an ice bath for 30 minutes. After the cold stir, the reaction was filtered and the filter cake was washed with cold ethyl acetate (3 mL). The filter cake was vacuum dried at 40° C./5 Torr affording 940 mg (83%) of the title compound as a white solid. mp 169° C.–170° C. EA calculated for $C_{28}H_{39}N_5O_7S$: C, 57.03; H, 6.67; N, 11.88; O, 18.99; S, 5.44. Found: C, 57.26; H, 6.45; N, 11.86; O, 18.73; S, 5.74.

The present invention has been described in detail, including the preferred embodiments thereof. However, it will be appreciated that those skilled in the art, upon consideration of the present disclosure, may make modifications and/or improvements that fall within the scope and spirit of the invention as set forth in the following claims.

Although the compounds of formula III and III(a) have been pictured throughout this specification as having only one particular orientation about their two double bonds, all possible isomers are encompassed within the scope of this invention.

What is claimed is:
1. A process for preparing a compound of formula IV:

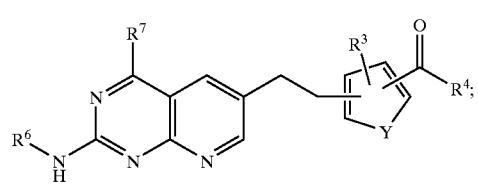

where:
Y is CH=CH, O, or S;
R$^3$ is hydrogen, chloro, or fluoro;
R$^4$ is hydroxy, a carboxy protecting group, or NHC*H(C(O)R$^5$)CH$_2$CH$_2$C(O)R$^5$ where the configuration about the carbon atom designated * is S; and
R$^5$ is hydrogen or a carboxy protecting group;
R$^6$ is hydrogen or an amino protecting group; and
R$^7$ is hydroxy or amino; or
a salt or solvate thereof;
comprising:
a) reacting a compound of formula III(a):

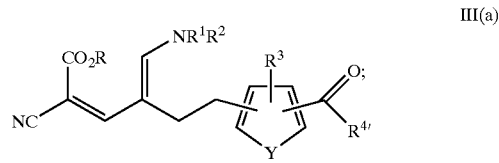

where:
R is C$_1$–C$_6$ alkyl;
R$^1$ and R$^2$ are independently C$_1$–C$_6$ alkyl or taken together with the nitrogen to which they are attached form a heterocycle;
R$^{4'}$ is a carboxy protecting group or NHC*H(C(O)R$^{5'}$)CH$_2$CH$_2$C(O)R$^{5'}$ where the configuration about the carbon atom designated * is S; and
R$^5$, is a carboxy protecting group;
with 2,4-diamino-6-hydroxypyrimidine in the presence of a suitable acid and solvent;
b) optionally installing an amino protecting group at R$^6$; and
c) optionally removing any carboxy protecting groups at R$^{4'}$.

2. A process according to claim 1 where the compound of formula IV is a compound where R$^7$ is hydroxy, Y is CH=CH or S, and R$^3$ is hydrogen; or a salt or solvate thereof.

3. A process according to claim 1 where the compound of formula IV is a compound where R$^7$ is hydroxy, Y is CH=CH or S, and R$^3$ is hydrogen, or a salt or solvate thereof; the compound of formula III(a) is a compound where R$^{4'}$ is methoxy, ethoxy, or benzyloxy, or a salt or solvate thereof; and step c) is performed.

4. A process according to claim 3 where the compound of formula IV is a compound where R$^6$ is 2,2-dimethyl-1-oxopropyl; or a salt or solvate thereof.

5. A process according to claim 1 where the acid is acetic acid and the solvent is acetonitrile.

6. A process for preparing a compound of formula IV:

IV where:
Y is CH=CH, O, or S;
R³ is hydrogen, chloro, or fluoro;
R⁴ is hydroxy, a carboxy protecting group, or NHC*H(C(O)R⁵)CH₂CH₂C(O)R⁵ where the configuration about the carbon atom designated * is S; and
R⁵ is hydrogen or a carboxy protecting group;
R⁶ is hydrogen or an amino protecting group; and
R⁷ is hydroxy or amino; or a salt or solvate thereof;
comprising:
a) reacting a compound of formula V(b):

where:
R⁴' is a carboxy protecting group or NHCH(C(O)R⁵', CH₂CH₂C(O)R⁵'; and
R⁵' is a carboxy protecting group; or a salt or solvate thereof;
with an oxidizing reagent in the presence of a suitable solvent; and
b) optionally removing any carboxy protecting groups at R⁴' and/or at R⁶;
with the proviso that if R⁶ is hydrogen in the compound of formula V(b) then the compound of formula V(b) must be an acid addition salt.

7. A process according to claim 6 where the compound of formula IV is a compound where Y is CH=CH or S and R³ is hydrogen; or a salt or solvate thereof.

8. A process according to claim 7 where the compound of formula V(b) is a compound where R⁴' is NHC*H(C(O)R⁵')CH₂CH₂C(O)R⁵', R⁵' is C₁–C₆ alkyl; R⁶ is an amino protecting group; and R⁷ is hydroxy; or a salt or solvate thereof.

9. A process according to claim 8 where the compound of formula V(b) is a compound where R⁵' is methyl or ethyl and R⁶ is 2,2-dimethyl-1-oxopropyl; or a salt or solvate thereof.

10. A process according to claim 6 where the oxidizing reagent is 2,3-dichloro-5,6-dicyano-1,4-benzoquinone and the solvent is dichloromethane.

11. A process for preparing a mixture comprising compounds of formula V(f)(R) and V(f)(S):

V(f)(R)

+

V(f)(S);

where:
Y is CH=CH or S;
the configuration about the carbon atom designated * is S;
R⁵' is a carboxy protecting group; and
R⁶' is an amino protecting group; or a salt or solvate thereof;
comprising:
a) reacting a compound of formula V(b):

V(b)

with an oxidizing reagent in the presence of a suitable solvent;
b) optionally removing any carboxy protecting groups and amino at R⁵' and/or any amino protecting groups at R⁶'; and
c) hydrogenating a compound of step b) to form a mixture comprising compounds of formula V(f)(R) and V(f)(S) or a salt or solvate of each thereof.

\* \* \* \* \*